(12) United States Patent
Croud et al.

(10) Patent No.: US 8,906,698 B2
(45) Date of Patent: Dec. 9, 2014

(54) METHOD AND APPARATUS FOR MEASURING FLUORESCENCE IN LIQUIDS

(75) Inventors: Vincent Brian Croud, Sheffield (GB); Duncan William John McCallien, Darlington (GB); Ian Stuart Edworthy, Washington (GB)

(73) Assignee: Johnson Matthey PLC, London (GB)

( * ) Notice: Subject to any disclaimer, the term of this patent is extended or adjusted under 35 U.S.C. 154(b) by 376 days.

(21) Appl. No.: 13/147,519

(22) PCT Filed: Feb. 2, 2010

(86) PCT No.: PCT/GB2010/050159
§ 371 (c)(1),
(2), (4) Date: Oct. 17, 2011

(87) PCT Pub. No.: WO2010/089587
PCT Pub. Date: Aug. 12, 2010

(65) Prior Publication Data
US 2012/0034702 A1 Feb. 9, 2012

(30) Foreign Application Priority Data

Feb. 3, 2009 (GB) .................................. 0901658.5

(51) Int. Cl.
*G01N 21/76* (2006.01)
*G01N 33/28* (2006.01)
*G01N 21/64* (2006.01)

(52) U.S. Cl.
CPC .......... *G01N 21/643* (2013.01); *G01N 33/2882* (2013.01); *G01N 2021/6432* (2013.01)
USPC ..................... 436/172; 422/82.08; 250/458.1; 250/459.1

(58) Field of Classification Search
None
See application file for complete search history.

(56) References Cited

U.S. PATENT DOCUMENTS

| | | | |
|---|---|---|---|
| 2,392,620 | A | 1/1946 | Sparks |
| 4,659,676 | A | 4/1987 | Rhyne, Jr. |
| 4,735,631 | A | 4/1988 | Orelup |
| 5,358,873 | A | 10/1994 | Nowak |

(Continued)

FOREIGN PATENT DOCUMENTS

| | | |
|---|---|---|
| CN | 1513118 | 7/2004 |
| GB | 2335978 | 10/1999 |
| WO | 2005052560 | 6/2005 |

OTHER PUBLICATIONS

International Search Report for PCT/GB2010/050159 dated Apr. 21, 2011.

(Continued)

*Primary Examiner* — Robert Xu
(74) *Attorney, Agent, or Firm* — RatnerPrestia

(57) ABSTRACT

A method of measuring the fluorescence of a fluorescent marker compound dissolved or dispersed in a bulk material includes: (a) measuring a characteristic of the fluorescence of a mixture of said bulk material and said fluorescent marker compound; (b) quenching the fluorescence of the fluorescent marker compound to produce a quenched mixture; (c) measuring the characteristic of the fluorescence of the quenched mixture; (d) comparing the fluorescent characteristic of the mixture with the fluorescent characteristic of the quenched mixture; and (e) correcting the measured fluorescent emission characteristic for the effects of the absorbance of the bulk material. The measurement may be further corrected to account for the absorbance of the material which is also known to have an effect on the measured fluorescence. A method of tagging and identifying a bulk material with a fluorescent marker compound, and an apparatus for carrying out the methods are also described.

14 Claims, 4 Drawing Sheets

(56) References Cited

U.S. PATENT DOCUMENTS

| | | |
|---|---|---|
| 5,387,527 A | 2/1995 | Sternberg |
| 6,127,133 A | 10/2000 | Akong |
| 2004/0248307 A1 | 12/2004 | Grof et al. |
| 2006/0264362 A1 | 11/2006 | Pitson et al. |
| 2007/0064323 A1 | 3/2007 | Luther |
| 2008/0274463 A1 | 11/2008 | Chen |

OTHER PUBLICATIONS

Holland et al., "A Unique Computer Centered Instrument for Simultaneous Absorbance and Fluorescence Measurements," Analytical Chemistry, vol. 45, No. 1, Jan. 1, 1973, pp. 145-153.

Great Britain Search Report for GB0901658.5 dated May 7, 2009.

International Preliminary Report on Patentability for PCT/GB2010/050159 dated Aug. 9, 2011.

Chinese OA dated Sep. 27, 2013 for Application No. 201080006575.4.

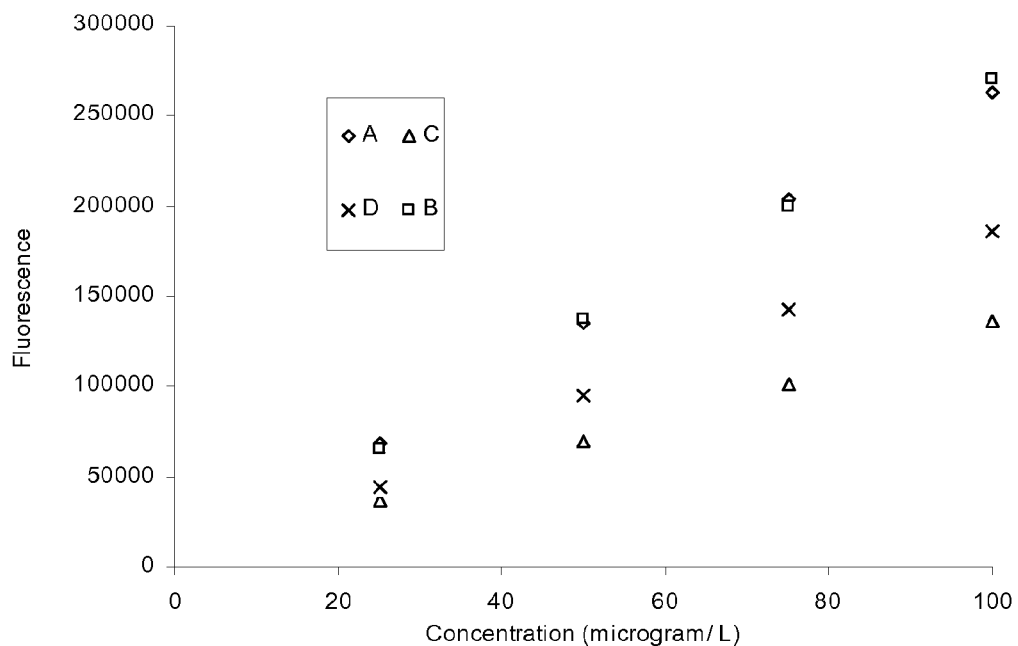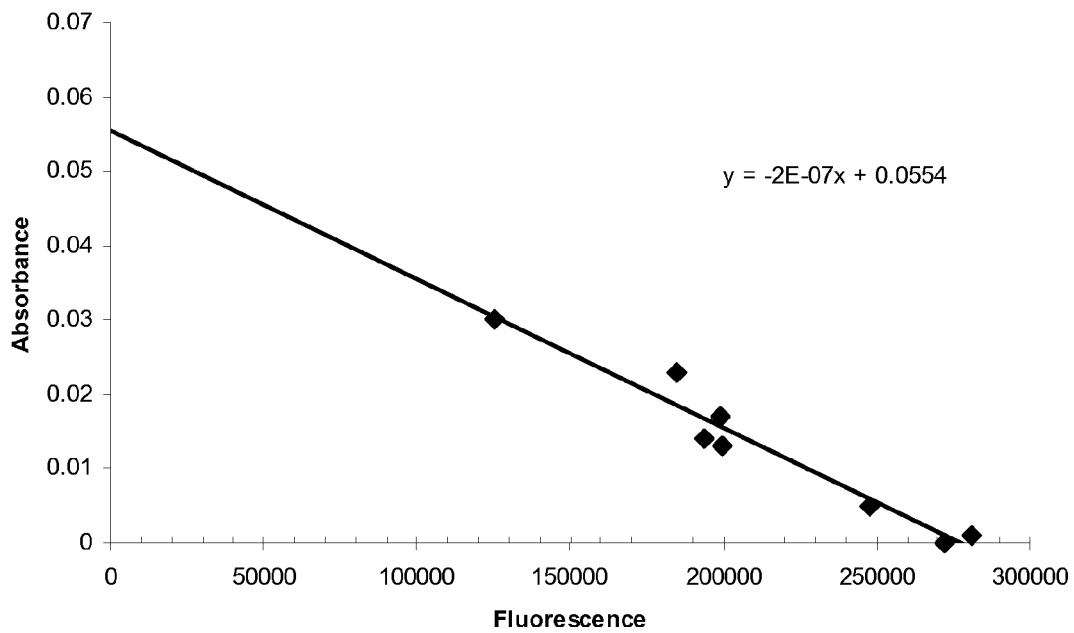

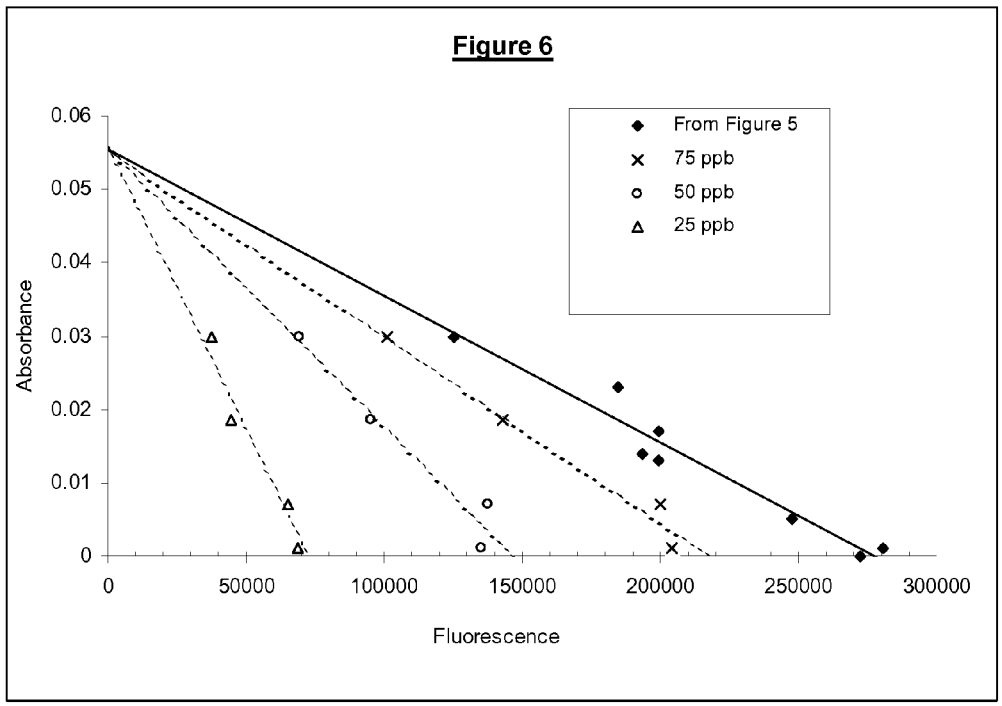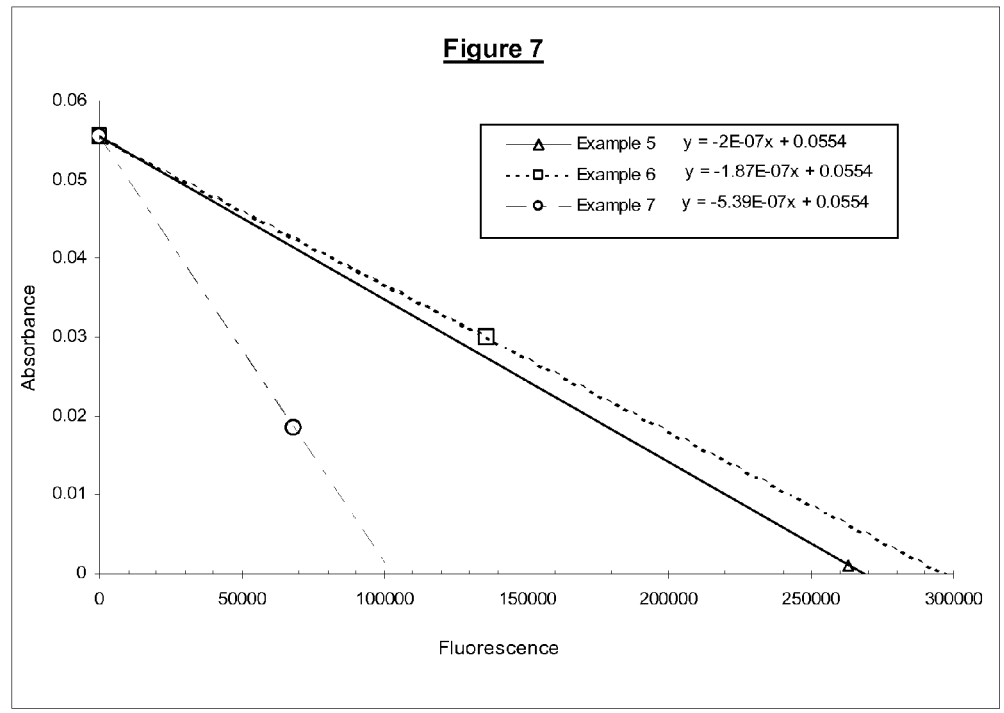

METHOD AND APPARATUS FOR MEASURING FLUORESCENCE IN LIQUIDS

CROSS-REFERENCE TO RELATED APPLICATIONS

This application is the U.S. National Phase application of PCT International Application No. PCT/GB2010/050159, filed Feb. 2, 2010, and claims priority of British Patent Application No. 0901658.5, filed Feb. 3, 2009, the disclosures of both of which are incorporated herein by reference in their entireties for all purposes.

FIELD OF THE INVENTION

The present invention is concerned with the measurement of fluorescence, in particular for the identification of fluorescent compounds present in liquids.

BACKGROUND OF THE INVENTION

The use of fluorescent dyes as markers or tags for liquid and solid materials is well known. A typical application is the tagging of liquids such as hydrocarbon fuels in order to identify the liquid at a subsequent point in the supply chain. This may be done for operational reasons, e.g. to assist in distinguishing one grade of fuel from another, or for other reasons, in particular to ensure fuel quality, deter and detect adulteration and to provide a means to check that the correct tax has been paid. Apart from fuels, other products, such as vegetable oils may be marked to identify the product produced at a particular source, or certified to a particular standard.

A problem with the method of detecting fluorescent compounds used as markers arises when the material which is marked interferes with the fluorescence of the marker by absorbing the excitation or emitted light, by exhibiting its own background fluorescence, or by changing the fluorescent characteristics of the marker. This is a particular problem in the marking of coloured liquids, such as petroleum derived products, with fluorescent dyes. Hydrocarbon based liquids, such as fuels, exhibit a broad fluorescent emission. The fluorescent background tends to add to any fluorescent signal of the dye but the inherent absorbance of the liquid diminishes the fluorescence of the dye. The marking of such fuels, especially gasoline and diesel, is an important use of marker compounds and the ability to detect single or multiple marker compounds with a high degree of certainty is critical to the use of such markers in such valuable and widespread products. The problem has been addressed in many ways, most of which involve the separation of the marker compound from the liquid by means of extraction into a polar liquid or onto a solid absorbent. For example, U.S. Pat. No. 5,358,873 describes and claims a method of detecting gasoline adulteration by tagging with a rhodamine dye and then shaking a small sample of the suspected fuel in a vial containing a small quantity of unbonded flash chromatography-grade silica. The presence of the rhodamine marker dye in the suspect sample colours the silica red. U.S. Pat. No. 4,659,676 describes a fluorescently labeled complex hydrophobic fluid produced by dissolving therein a porphyrin. The fluorescently labeled complex hydrophobic fluid is identified by observation of the characteristic fluorescence upon irradiation. For identification purposes the porphyrin may be first extracted into an acidic aqueous solution for determination of fluorescence. U.S. Pat. No. 2,392,620 describes the use of umbelliferone or a derivative as a fluorescent marker for petroleum with detection by determination of the characteristic fluorescence after extraction into an aqueous alkaline solution. In U.S. Pat. No. 4,735,631, fuels are marked with certain substituted anthraquinones which are subsequently detected in a marked sample of fuel by extraction into an immiscible alkaline reagent.

SUMMARY OF THE INVENTION

The present invention provides a method for determining the presence of a fluorescent material which overcomes at least some of the disadvantages of such prior methods.

According to the invention, we provide a method of measuring the fluorescence of a fluorescent marker compound dissolved or dispersed in a bulk material comprising the steps of:
  (a) measuring a characteristic of the fluorescence of a mixture of said bulk material and said fluorescent marker compound;
  (b) quenching the fluorescence of the fluorescent marker compound to produce a quenched mixture;
  (c) measuring the characteristic of the fluorescence of the quenched mixture;
  (d) comparing the fluorescent characteristic of the mixture with the fluorescent characteristic of the quenched mixture; and
  (e) correcting the measured fluorescent emission characteristic for the effects of the absorbance of the bulk material.

According to another embodiment of the invention, we provide an apparatus suitable for use in carrying out the method of any one of the preceding claims, said apparatus comprising:
  (a) at least one excitation light source which is capable of emitting light of a wavelength selected to be a wavelength which excites detectable fluorescence in at least one of the fluorescent marker compounds;
  (b) at least one light detecting device for detecting fluorescent light emitted by said at least one fluorescent marker compound;
  (c) at least one absorbance light source which is capable of emitting light of a wavelength selected to be a wavelength which does not excite detectable fluorescence of any of the fluorescent marker compounds but which is absorbed by the bulk material;
  (d) at least one light detecting device for detecting light emitted by said absorbance light source which is transmitted through the sample;
  (e) data processing means for calculating information required by the user concerning the corrected fluorescence of the sample; and
  (f) control means for controlling at least a part of the operation of the apparatus.

By comparing the measured fluorescence of the mixture with that of the quenched mixture, the difference may be attributed to the fluorescence of the marker compound so that an indication of the nature or concentration of the marker compound in the mixture may be estimated in the presence of the bulk material without relying on a separation step. Although the separation of a fluorescent compound prior to measuring its fluorescence is useful for establishing the presence and identity of the compound through its characteristic fluorescence, a separation step may introduce uncertainty into any attempt to quantify the amount of the compound originally present in the bulk material.

Accordingly, a method of identifying a bulk material comprises the step of adding to said bulk material a marker comprising at least one fluorescent compound to form a mixture of said bulk material and the fluorescent marker compound and, subsequently, measuring the fluorescence of said at least one fluorescent compound using the method of measuring fluorescence of the invention.

The bulk material may be solid or liquid, but is preferably a liquid. The liquid may be organic or aqueous and may comprise one or more dissolved or dispersed ingredients. The material is usually a commercial product to which a marker compound is added in order to identify it at a later point in the supply chain or in an industrial process. Such products include fuels such as petroleum and petroleum derived products, in particular gasoline, diesel, kerosene, lubricating oils ethanol, gasohols, greases and solvents and also bio-derived fuels such as oils derived from palm oil, jatropha, soya etc. The method may also be used to identify a marker compound in products such as perfumes, inks, varnishes and paint products.

The fluorescent compound is selected from the available compounds which have known fluorescent characteristics, i.e. which emit fluorescent light at an emission wavelength when illuminated with light of a different, shorter, excitation wavelength. In order to achieve the clearest resolution between the fluorescence due to the fluorescent compound and that of the bulk material, the difference between the excitation wavelength and emitted wavelength for the compound should be as different as possible from any species in the bulk material. In practice, the best way to achieve this distinction is to use a compound showing the greatest possible difference between the wavelength of the radiation used to excite it and the wavelength of any emitted radiation. It is preferable, but not essential, to use the excitation wavelength that will generate the maximum fluorescent emission and to detect at the wavelength corresponding to the most intense emission. The difference between the excitation and emission wavelengths is similar to, but not necessarily the same as, the difference between the wavelength of maximum absorption and wavelength of maximum fluorescent emission for the compound, which in turn is often described as the Stokes shift. In subsequent explanation, where reference is made to the Stokes shift of a compound any transitions not strictly corresponding to the Stokes shift, such as transitions involving other vibrational energy levels, sub-bands in the fluorescence spectrum or any transition resulting in a fluorescent emission will also be implied.

BRIEF DESCRIPTION OF THE FIGURES

The invention will be further described in view of the following non-limiting Figures, in which:

FIG. 4 is a plot of fluorescence versus concentration of Dye 1 in four fuels A-D.

FIG. 5 is a plot of the fluorescence emission of Dye 1 dissolved in eight different fuels at 100 µg/l versus absorbance of the fuels at 610 nm.

FIG. 6 is a plot of the fluorescence emission of Dye 1 dissolved in fuels A-D at 25, 50, 75 µg/l versus absorbance of the fuels at 610 nm.

FIG. 7 is a plot of the fluorescence emission of Dye 1 versus absorbance at 610 nm for Examples 5, 6 & 7.

DETAILED DESCRIPTION OF THE INVENTION

Typically the Stokes shift of a useful marker compound is at least 10 nm, more usually at least 20 nm and often at least 50 nm. When the bulk material is inherently fluorescent (e.g. gasoline and diesel) or contains one or more fluorescent compounds in its un-marked state, it is preferred, in one embodiment of the invention, to use a fluorescent marker compound having a larger Stokes shift than the bulk material itself. The excitation wavelength of the fluorescent marker compound usually lies within a range from the ultraviolet to infrared, i.e. from about 200-1200 nm.

Preferred fluorescent compounds include fluorescent dyes having an excitation and emission wavelength between about 350-850 nm. Such dyes may absorb light in the visible region, i.e. they may be visibly coloured, although when used in a coloured bulk liquid or at very low concentration, they may not be visible when mixed with the bulk material.

Figure 1:
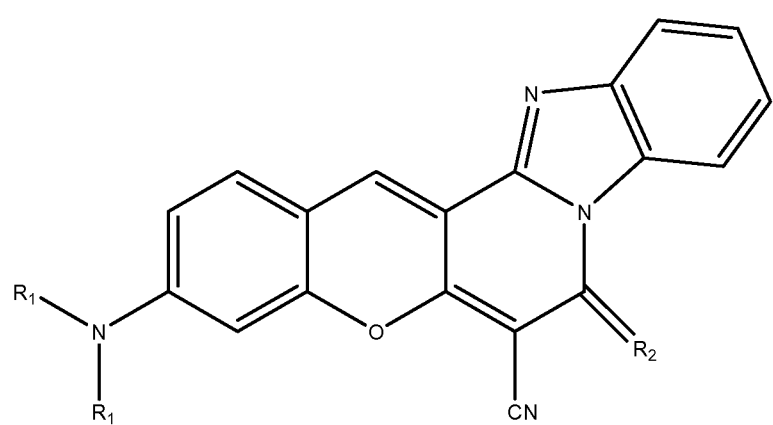
FIG. 1 shows the chemical structure of a suitable class of fluorescent compound.

Suitable fluorescent materials include any which have been described in the prior art for use as fluorescent markers and other compounds which are found to be suitable for such uses. In particular we mention phthalocyanines, naphthalocyanines, nickel dithiolenes, aminium compounds, methine dyes, azulene quadratic acid dyes, fluorescein and derivatives thereof, substituted anthraquinones, azo dyes, porphyrins, coumarin, substituted coumarins (including umbelliferones), benzopyrans and derivatives thereof, xanthene dyes (including rhodamines), oxazines, croconium dyes, naphthalimides, naphthofluorones, seminaphthofluorones, tricarbocyanines, bisindolylmaleimides, 1,3-diaryl- and 1,3,5-triaryl-2-pyrazolines, acridines, phenanthridines, dipyrromethenes. A class of suitable dyes, based on a substituted benzopyran, is shown in FIG. 1, where $R_1$ is an alkyl substituent which may be fused to the aryl ring adjoining the amino substituent; $R_2$ may be an imino or a carbonyl group. In one preferred example of this class, $R_1$ is a butyl substituent and $R_2$ is an imino group. The above list, which is not intended to be limiting, describes a very wide range of classes of fluorescent compounds which may be used in the method of the invention, provided there exists means for quenching the fluorescence of the compound when present in the bulk material. The fluorescent compound is also selected to be compatible with the bulk material so that it may be dissolved or dispersed therein in the concentration required for marking the material. Therefore the compounds may be used in ionic forms, where available, for use in polar liquids or derivatised to improve compatibility with and solubility in various organic liquids. The compound may be selected to be visible in the bulk material, e.g. to show that the material is marked, or alternatively it may be selected to be invisible to the eye in the bulk material, i.e, it may be a "silent" marker. Other criteria for selecting an appropriate fluorescent compound include its toxicity, cost, availability and stability in the bulk material. It is advantageous if one or more fluorescent dyes used as fluorescent marker compounds are present in the bulk material at a concentration at which the dye does not affect the measured absorbance associated with the bulk material. Preferably the fluorescent response of the dye at low concentrations is proportional to the concentration regardless of the colour of the medium.

Quenching the fluorescence may be achieved by physically treating the mixture, for example by heat, or by chemically treating the mixture, for example by changing the pH of the mixture, changing the polarity of the solvent, adding 'bleaching' agents such as oxidants or reductants or a chemical quenching compound. Quenching the fluorescence of the fluorescent compound changes its fluorescent characteristics. By "change" we include a change of either excitation or emission wavelength and/or a change in the amount of fluorescent light emitted. Usually quenching reduces the amount of fluorescence, as measured by the height of the emission peak in the fluorescence spectrum and often the peak is diminished to less than 20% of its height in the unquenched mixture. The fluorescent compound may be regarded as being completely quenched when its fluorescent emission peak height, when stimulated using light at a wavelength within +/−5 nm of its excitation wavelength, is not distinguishable from a typical variation in instrument response when measuring the bulk material in the absence of fluorescent compound. It is not necessary for the fluorescence from the fluorescent compound to be completely quenched, but it is preferable to quench substantially completely.

The means of quenching must be selected according to the fluorescent marker used. A quenching compound reacts with the fluorescent compound to change its fluorescent characteristics. The reaction may be by ion-pair association, complexation, a change of molecular configuration such as may be brought about by a change of solvent, oxidation of the chromophore, the creation of insoluble, non-fluorescent species or by other means. Suitable quenching compounds depend on the nature of the fluorescent compound. Known quenching agents for some well-known fluorescent dyes, such as xanthene, thioxanthene, perylene and benzopyran derivatives, include but are not limited to polyoxometallate salts (e.g. phosphomolybdic acid, phosphotungstic acid, tungstosilicic acid, tungstomolybdic acid); potassium thiocyanate (optionally in conjunction with an ion transfer reagent), N-chlorosuccinimide, amines such as tris-2-aminoethylamine and diazabicyclooctane, tetrabutylammonium hydroxide solution, trichlorocyanuric acid, peracetic acid, peroxides such as hydrogen peroxide and benzoylperoxide, anilines such as N-methylaniline and N,N-dimethylaniline, nitrobenzenes such as 1,3-dinitrobenzene, soluble transition metal complexes, chlorine and hypochlorite species. Preferred quenching agents for use in non-polar media, such as hydrocarbon fuels, are polar solutions of the polyoxometallate salts, especially in alcohol-based solutions. When added at high ppm quantities these instantaneously substantially quench the fluorescence of the dyes but leave the fluorescent response of the bulk liquid unchanged.

WO 2005/052560 describes the removal of a fluorescent dye from a liquid mixture by absorbing the dye onto an absorbent material so that the optical density of the liquid sample may be measured to enable a correction to be applied to the measured emitted fluorescence of the liquid sample containing the dye, based upon the optical density of the liquid medium in the absence of the dye. Removal of the dye from the bulk material using an absorbent is much more labour intensive than quenching the dye in-situ as it relies upon elution onto, and then from, the separation cartridge and then a subsequent accurate dilution to a known volume. The method of WO 2005/052560 is therefore excluded from the present invention.

The fluorescent emission from the unquenched mixture is corrected by comparing it with the fluorescent emission from the quenched mixture. This determines the amount of fluorescence arising solely from the one or more fluorescent tags in solution. In a preferred embodiment, the emission spectrum of the quenched mixture is subtracted from that of the unquenched mixture. It is further preferred to correct for the effect of absorption of light by the bulk material. The corrected emission spectrum is used to determine the fluorescent characteristics of the sample tested. One or more of these characteristics (e.g. the wavelength and/or magnitude of fluorescent emission) may then be compared with the similar characteristics obtained from a standard sample of the mixture containing a known amount of the fluorescent marker in a medium of known colour and background fluorescence. A discrepancy between the emission detected from the measured sample and that from the standard sample is then indicative that the bulk material from which the sample was taken has been changed, e.g. diluted or otherwise tampered with. The characteristics of a standard sample may be recorded and used as a simple numerical comparison with the measured sample.

We have found that the fluorescent response of a dye usually varies approximately linearly with the colour of the medium in which the dye is dissolved once the effect of the fluorescent background of the medium has been taken into account. This is due to the absorption by the medium of either or both of the excitation light and the emitted fluorescent light. This is particularly relevant when the material to be marked is a coloured liquid such as a hydrocarbon fuel, which may exhibit significant colour variations in the same product and which can also change colour naturally over time. In a preferred form, the method of the invention enables appropriate correction of the fluorescent response (amount of fluorescence, excitation or emission wavelength) after correction for the background fluorescence of the medium (i.e. the bulk material) and also taking into account its colour. The corrected fluorescent response may then be converted into a concentration of dye, using a calibration. We have also confirmed the observations behind the Lippert-Mataga equation that the degree of fluorescence is dependent upon the polarity of the medium that it is dissolved in. This means that the correlation of fluorescence with absorbance should ideally be made only on liquids with similar polarities. If a fluorescent marker is used that is little affected by the polarity of the solvent then the data for gasoline and diesel based fuels can be compared on the same plot. It is therefore preferred to use fluorescent markers which are less sensitive to variations in the polarity of the medium in which they are dispersed. If a fluorescent marker is used that is strongly affected by the polarity of the solvent then it is preferred to compare the results for gasoline based fuels only with other gasoline based fuels, i.e. separately from diesel based fuels. If fluorescent markers are used which have a strongly solvent dependent fluorescence then the polarity of the medium should be standardised by the addition of another solvent prior to any analysis.

The fluorescence of the quenched and unquenched mixture is measured by irradiating a sample of the mixture with light of a wavelength which excites fluorescent emission of the fluorescent marker compound. This may be done using a standard fluorimeter in which a sample, normally contained in a transparent cell or cuvette, is irradiated with light of known wavelength (the excitation radiation). By transparent, we mean that the sample cell, or at least a portion of it, is substantially transparent to the excitation radiation and the emitted fluorescence. The light emitted by the sample is then collected using a light detecting device and the wavelength and intensity of the emitted light are measured. The excitation radiation is usually of a pre-determined wavelength which is chosen to be of a wavelength which is capable of being absorbed by and producing fluorescent emission from one of the fluorescent materials in the sample. The wavelength selected for the excitation radiation depends upon the shape of the absorption peak of the particular fluorescent marker compound in use. The excitation wavelength may be a range of wavelengths within which the dye is stimulated to fluoresce. The excitation wavelength is preferably less than or about equal to the wavelength of maximum absorption in order to avoid detection of the excitation radiation and interference with the fluorescence emission spectrum. The wavelength selected for the excitation radiation may depend upon the shape of the absorption peak of the particular fluorescent compound in use. The excitation radiation may be produced by any known source, e.g. a full-spectrum light source with a suitable band-pass filter or diffraction grating or, by a single or narrow-band source such as a laser. Laser light sources are available at many different wavelengths and may be selected or tuned to provide light of the correct wavelength to excite fluorescence in at least one of the fluorescent materials. A particularly suitable light source comprises an LED, selected to emit light of the desired intensity and spectrum. It is preferred to provide a separate light source for each fluorescent marker material present in the sample, each being selected and tuned or filtered to emit radiation at or near the frequency of maximum absorption of a respective fluorescent marker. When more than one light source is present, means are provided to indicate to the data-processor which radiation source is being used. The radiation emitted by the source should ideally have a centre peak wavelength which does not vary by more than ±2 nm over the period of time taken to test the sample in order to ensure that the absorption spectrum does not vary. When using a light source which produces output radiation whose wavelength varies with temperature, for example, then a stabilised source should be selected, and temperature stabilising means such as a Peltier module or alternative heat-sink should be provided. The temperature stabilizing means may also be useful to warm the light source if necessary to bring the source to its optimum operating temperature. It is possible to divert a portion of the excitation radiation directly to a radiation detector in order to determine the centre peak wavelength and/or the intensity of a particular wavelength of the emitted light and its variability. Where the centre peak wavelength or the intensity of a particular wavelength of the excitation radiation changes between samples, it may be possible to calculate an enhancement or reduction factor for the sample fluorescence spectrum to compensate for changes in the excitation radiation which cause the sample to absorb more or less energy.

In order to differentiate between light transmitted through the sample and fluorescent emission by the sample, it is usual to place the light detector out of the path of transmitted light. The light detector may be a photocell or photodiode, including a charge-coupled device. The emitted radiation from the sample may be directed into the path of the radiation detector by one or more lenses or mirrors or a combination thereof as is known to the skilled person. It is preferred that the emitted radiation is collected over the whole of the path length of the sample for maximum sensitivity to changes in the emission between samples. The radiation may pass through a slit or aperture to reduce the divergence of light reaching the detector and thus increase the resolution of the spectrum. The aperture is preferably of similar dimension to the path length. The detector may be any of those used in standard spectroscopy apparatus, including, for example, a photocell, a charge-coupled device etc. Normally the radiation emitted from the sample is split into individual wavelengths, e.g. by a diffraction grating, a prism or a concave holographic mirror and the intensity of the light at each wavelength is then measured by the detector. The optical system comprising the mirror, lenses, diffraction grating and detector are preferably designed as a close-coupled optical system.

The apparatus according to the invention is also provided with means for measuring the absorbance of the medium in addition to the optics for measuring the fluorescence of the sample described above. The absorbance of the medium should be measured using a light source, referred to hereinafter as an "absorbance light source", which does not cause the dye to fluoresce. In practice, this light source should either be too weak to cause any dye present to fluoresce to an extent which is measurable by the light detector, or the light source should produce light that is at a wavelength that causes no measurable fluorescence to occur for any of the dyes present. The absorbance light source may comprise one or more filters in order to produce the desired characteristics for measuring the absorbance of the medium. As will be appreciated, the absorbance of the sample is calculated by referencing the amount of light transmitted through the sample with the light transmitted through a colourless reference standard, the absorbance of which is taken to be "zero absorbance" and which is measured during calibration of the instrument. The absorbance, by the sample, of light emitted from the absorbance light source may be measured by the same light detector used to measure a fluorescent emission from the sample. Alternatively a separate detector may be used to measure absorbance.

A preferred apparatus comprises an instrument for measuring fluorescence and absorbance which has two or more light sources and one or more detectors. All but one of the light sources are "excitation" light sources, suitable for emitting light at a wavelength which excites the one or more fluorescent compounds to fluoresce. In a preferred embodiment, each such light source comprises an LED arranged in combination with a suitable band-pass filter. The fluorescent light emitted by the sample (if any) is detected by the one or more detectors situated out of the path of the transmitted light, preferably at about 90° to the path of the transmitted light. The other, "absorbance light source" is chosen to cause no fluorescence but is situated so as to emit light directly towards a light detector arranged to measure the light transmitted through the sample, which may be one of the light detectors used for measuring a fluorescent emission. The light emitted by the absorbance light source should be incapable of causing excitation of the dye but capable of being absorbed by the medium. In a preferred embodiment of the apparatus, the absorbance light source is an LED selected to emit white light but of relatively low intensity compared with the light sources provided to excite fluorescence. This absorbance light source and its detector are together used for determining the absorbance of the medium. By a suitable arrangement of the electronics associated with the instrument, a shared detector, i.e. a detector which is used to detect absorbance or transmittance and fluorescence, can be operated so as to determine whether it is detecting transmitted light from the absorbance light source or light emitted by fluorescence. Such an arrangement may include synchronising the detector with the timing of activating the "fluorescence exciting" light source(s) and the "absorbance" light source. Alternative arrangements may rely on distinguishing between the transmitted light used for the absorbance measurement and the fluorescent light, used for the fluorescence measurement by the difference between the wavelengths of transmitted light and the wavelengths of fluorescent light. This shared detector can therefore be used to collect data suitable for both absorbance and fluorescence measurements.

The data from the detectors is collected and analysed using a data processor which produces the information required by the user concerning the corrected fluorescence of the sample. The data processor is preferably programmed to compare the fluorescence of the quenched mixture with that of the unquenched mixture and preferably to compensate for the absorbance of the medium and also to make the appropriate calculations to produce a subtraction, difference or aggregate spectrum. The calculations may operate on only one or a few data points, e.g. the peak height at a particular wavelength rather than a whole spectrum. When the user requires information concerning the light emitted at each wavelength, the data processing device may produce this information in the form of a chart or graph etc. The data processor may be linked to a data storage device so that information on previous plots may be retrieved and compared.

A control means controls the operation of the apparatus, at least in part. The control means ensures activation of the appropriate light source at the appropriate time and for an appropriate duration according to the measurement method used. The control means may also provide automatic or semi-automatic operation of the apparatus in response to a user interface. For example, semi-automatic operation may comprise the generation of information and instruction messages to prompt the user to operate or manipulate a part of the apparatus or change or insert a sample. The control means and data processor are conveniently provided as a suitably programmed electronic microprocessor.

The measurement apparatus is preferably portable, having all components located within a single housing. Preferably suitable means are provided to assist its portability such as one or more handles, straps or other carrying means, as required. Controls are provided to open/close the sample holder and operate the instrument to allow light from the selected radiation source to enter the sample. The housing preferably also comprises a power source such as a battery pack or a power adapter. The power source may, however, be provided in a separate housing so that heat generated by the power source may be dissipated without affecting the temperature of the apparatus. The housing may incorporate a display to indicate the results from a sample, the status of the instrument or instructions and information as to its method of use. The indication means may comprise a screen, message display or some other indicator such as a light.

The method of using the apparatus of the invention comprises a calibration step. In the calibration step, a cuvette or sample cell containing a colourless liquid, such as water or a colourless organic solvent, is placed in the sample holder and the transmission of light from the "absorbance light source" is measured to determine the absorbance of the liquid. This value is then recorded as "zero absorbance" for the calibration. As a further calibration, samples of light and dark liquids similar to the samples to be measured, each containing either no tag (or a quenched tag) or a standard amount of unquenched taggant are introduced sequentially into the sample holder and the fluorescence is determined. The measured fluorescence is then used to calibrate the instrument so that the difference between the fluorescence measurement from a tagged sample and an untagged (or quenched) sample is known for the particular apparatus, both for light-coloured liquids and dark-coloured liquids. We have found that the calibration for zero absorbance (using a colourless liquid) is preferably repeated daily or weekly, depending on the usage of the apparatus, or before each unknown sample measurement or batch of such measurements. The calibration using light and dark liquids should be carried out each time there is a significant change in the nature of the samples to be measured, for example when changing between gasoline and diesel samples, or when the colour or polarity of the samples varies significantly from those of the calibration liquids. The calibration enables the data processor to calculate a relationship between the absorbance of the calibration samples and the fluorescence of the standard known tags in the calibration samples. This calibration may then be used to adjust the measured fluorescence of subsequent samples to correct for the effect of the sample colour on the measured fluorescence of the tag. A method of calculating the correction is shown in the Examples. In this method, the calibration indicates the calculated fluorescence of the calibration samples in a sample of zero absorbance, by extrapolation. Using the calibration, the fluorescence measured from each sample can then be adjusted to a value calculated at zero absorbance so that the effects of colour can then be ignored in calculating the amount of tag present from the fluorescence emitted by the coloured sample.

After calibration, the method of using the instrument preferably comprises the following steps. A sample of liquid containing an unknown amount of tag (an "unknown" sample) is placed in the sample holder. The instrument determines the fluorescence of the sample by causing one or more of the fluorescence-exciting light source(s) to illuminate the sample and by measuring the fluorescent light emitted by the sample which is detected by one or more of the light detectors. This fluorescent light spectrum (or part of the spectrum) is recorded, e.g. as "spectrum A". The instrument also determines the absorbance of the sample by illuminating the sample with light from the "absorbance" light source and measuring the amount of light transmitted through the sample measured by the detector which is arranged to detect the transmitted light. The apparatus then measures the fluorescence of a sample of the unknown liquid which has been treated to quench the fluorescence of the tag. This sample may be the same sample as the one previously measured, following subsequent treatment to quench the fluorescence, or a second sample of the same unknown liquid which has been treated to quench the fluorescence of the tag. This fluorescent light spectrum (or part of the spectrum) is recorded, for example, as "spectrum B". The apparatus then calculates the fluorescence, i.e. the amount of light emitted at one or more of the fluorescent wavelengths of the tag, due solely to the tag, by subtracting the recorded spectrum (or part spectrum) B from the recorded spectrum (or part spectrum) A, or by any other appropriate means by which the difference in fluorescence may be ascertained. When we refer to "part of the spectrum" we mean that the full spectrum need not be measured or recorded because in many cases it may be necessary to measure and/or record only the part of the spectrum falling between certain predefined wavelengths because the fluorescent characteristics of the tag will be known. The part spectrum may include the wavelengths between which a characteristic peak of fluorescence occurs or it may be still narrower than the spectrum of an entire peak.

The user may be required to place each sample in the sample holder before each measurement. Alternatively, the user may place a sample of unquenched and quenched sample in a sample holder which is adapted to hold more than one sample.

Such a sample holder may also be adapted to hold a sample of a standard colourless liquid for calibration of "zero absorbance". The appropriate sample may be moved into or out of the path of the light from the or each light source as required. As a further alternative, the apparatus may divert the light from the fluorescence-exciting light source and/or the absorbance light source through each sample by operation of mirrors or by alternative means. The apparatus may alternatively include a suitable number of light sources or means to split the light from the light sources into a suitable number of beams by which more than one sample may be illuminated simultaneously. The apparatus may be operated fully manually, automatically or semi-automatically. In semi-automatic operation, the operator takes such manual actions as are required, e.g. to change the sample which is illuminated, in response to a prompt generated by the control system of the apparatus.

The marker composition may comprise one or more than one fluorescent material. Preferably more than one fluorescent material is present, for example from 1 to 4 fluorescent materials, each being present in the marker composition in a known amount which may be different from the amount of each other material in the composition. Other materials may also be present, such as a solvent, other types of marker compound, non-fluorescent dyes etc. The marker composition is added to the liquid in a predetermined amount which contains a known amount of each fluorescent material contained within the composition. The marker composition may be supplied in a container containing a measured amount of the composition, calculated to provide a selected concentration of the or each fluorescent material when dissolved in a measured amount of the liquid.

EXAMPLES

The invention will be further described in the non-limiting Examples below, in which emission spectra were recorded on a Jobin Yvon Fluoromax-3 fluorescence spectrophotometer at an excitation wavelength of 510 nm using a 2.0 nm bandwidth, recording the emission at 610 nm. Ultraviolet and visible spectra were recorded on a Thermo Spectronic UV1 UV-Visible spectrophotometer with a 325 nm lamp and a 2.0 nm bandwidth. All measurements were made using a 10 mm cuvette. Dye 1, used in the following examples, is the compound shown in FIG. 1, where $R_1$ is a butyl substituent and $R_2$ is an imino group.

Example 1

The fluorescent emission spectra from an untagged sample of kerosene was recorded over the range 500-700 nm. The UV-Vis spectrum of the kerosene was also recorded from 400-900 nm using iso-octane as the reference solvent. A 100 microgram/liter (μg/l) solution of Dye 1 was prepared in 10 ml of the kerosene, to form a tagged kerosene. The fluorescence spectrum was recorded from 500-700 nm. 250 microliters of 12-molybdophosphoric acid (5 g/l in ethylhexanol) was added to the 10 ml sample of tagged kerosene in order to quench the fluorescence of Dye 1. After inverting the vial to ensure complete mixing, the fluorescence spectrum was again recorded from 500-700 nm.

Figure 2:
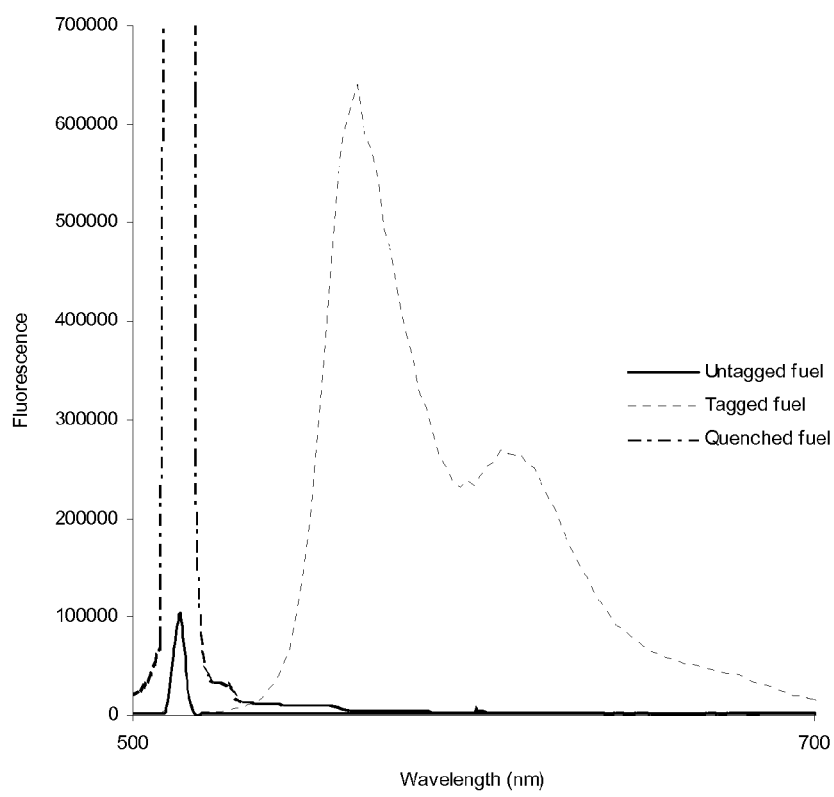
FIGS. 2 and 3 show the fluorescent emission spectra of untagged, tagged and quenched kerosene and motor spirit, respectively, as described in Examples 1 and 2.

The fluorescent emission spectra of the untagged, tagged and quenched kerosene are shown in FIG. 2. The fluorescent signal arising from the dye was quenched very effectively, with the resultant spectrum being very similar to that of the untagged fuel, especially around the wavelength used to measure the fluorescent emission of the dye The 'corrected' fluorescent emission of Dye 1 in kerosene may be regarded as the fluorescent emission of the dye plus background fluorescence of the fuel minus the fluorescent emission of quenched dye in the fuel. Hereinafter, "corrected fluorescence" should be taken to mean the difference between the fluorescent intensity at 610 nm of the unquenched sample containing Dye 1 and the fluorescent intensity at 610 nm of the quenched sample, i.e. after addition of the molybdophosphoric acid quenching agent.

Example 2

Figure 3:
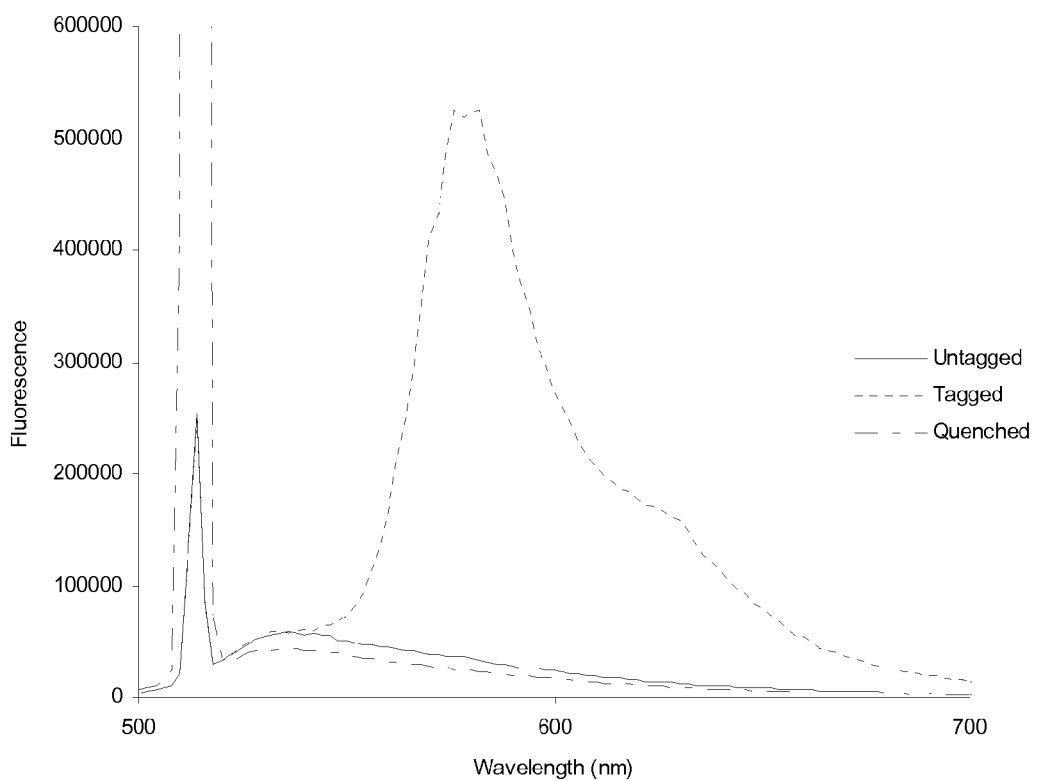

The experiment described in Example 1 was repeated using motor spirit. The fluorescent emission spectra of the untagged, tagged and quenched motor spirit are shown in FIG. 3. It can be clearly seen, by comparing the fuel containing no tag or quenched tag in FIG. 2 with the corresponding curves in FIG. 3, that the background fluorescence associated with the kerosene is far less than the background fluorescence associated with the motor spirit.

Example 3

Correlation of Fluorescence with Concentration

The fluorescent emission of Dye 1 was measured in four differently coloured fuels, designated A, B, C and D in FIG. 4. FIG. 4 shows the variation in fluorescent response with concentration for these fuels. In all of the fuels the fluorescent response of the dye is linearly proportional to its concentration at the dye concentration ranges considered. The effect seen in FIG. 4, that the fluorescent response of the dye at low concentrations is proportional to the concentration regardless of the colour of the medium, applies generally.

Example 4

Correlation of Fluorescence with Absorbance

The corrected fluorescent emission of Dye 1 was measured in eight differently coloured fuels using the method described in Example 1. The colour of each fuel was measured by measuring its absorbance at 610 nm. FIG. 5 is a plot showing the variation in corrected fluorescence of Dye 1 with absorbance for the eight fuels. In practice some of the least coloured fuels showed negative absorbances with reference to iso-octane, possibly due to a mismatch in refractive index between the fuel and the iso-octane. In order to simplify FIG. 5, the least-coloured fuel has been assigned zero absorbance and the absorbance values for the other fuels have been raised accordingly. It can be seen that the fluorescence varies linearly with the absorbance of the medium, assuming that the polarity of the different media are essentially the same. Knowing the variation in fluorescence with absorbance provides a method for calculating the amount of dye in a medium of arbitrary colour and arbitrary background fluorescence.

The line of best fit for the eight data points in FIG. 5 has equation:

$$\text{Absorbance} = -2.00 \times 10^{-7} \times \text{Fluorescence} + 0.0554 \qquad \text{Equation 1)}$$

This equation only applies to fuels containing 100 μg/l of dye. However, we know from FIG. 4 that the fluorescent response of the dye at below 100 μg/l is proportional to its concentration, regardless of the colour of the medium. FIG. 6 shows data for Dye 1 in the 4 different fuels used in Example 3 at 25, 50 and 75 ppb and it can be seen that all the correlations of fluorescent response with absorbance pass through the same point on the y-axis corresponding to the intercept of Equation 1.

In order to calculate the concentration of dye in an unknown sample we can only measure its fluorescence and absorbance. The other piece of information required is the y-intercept of Equation 1. This enables the generation of a new straight line, with y-intercept given by Equation 1 and which passes through the data point, for the unknown sample. The x-intercept of the new straight line corresponds to the fluorescent response of the unknown sample that would occur were the medium colourless, i.e. if the absorbance is zero. The x-intercept of Equation 1 corresponds to the fluorescence of 100 μg/l dye that would occur were the medium colourless. Therefore, by comparing the x-intercept of the new straight line calculated from the unknown sample with the x-intercept of Equation 1, given by samples containing 100 μg/l, we can calculate the concentration of dye in the unknown sample.

Example 5

The absorbance and fluorescence data for an unknown fuel were 0.001 and 263,000 respectively. Knowing that the intercept for the correlation of absorbance with fluorescence is a constant, given in Equation 1, then the gradient for a plot using this data would be $-2.00\times10^{-7}$, shown in FIG. 7. This would imply a fluorescent response in a colourless medium of 268,000. From the x-intercept of Equation 1 we can calculate a concentration of 0.097 mg/l dye. The actual level of dye was 100 μg/l, so the calculated value had an error of only 3%.

Example 6

The absorbance and fluorescence data for a second unknown fuel were 0.03 and 136,000 respectively. Using the y-intercept found from Equation 1, we can calculate a gradient for a plot using this data to be $-1.87\times10^{-7}$, shown in FIG. 7. This would imply a fluorescent response in a colourless medium of 296,500 or with reference to the x-intercept of Equation 1 a concentration of 0.107 mg/L dye. The actual level of dye was 100 μg/l and the fuel was Motor Spirit. This is an error of 7%. Simply comparing the fluorescence of the dye in Motor Spirit with the fluorescence of the dye in a medium of zero absorbance would have predicted a mere 0.050 mg/l for example 2 which is an error of 50%.

Example 7

The absorbance and fluorescence data for a third unknown fuel known to contain Dye 1 were 0.019 and 68,500 respectively. Knowing that the intercept for all correlations between absorbance and fluorescence is a constant, given in Equation 1, then the gradient for a plot using this data would be $-5.39\times10^{-7}$, shown in FIG. 7. This would imply a fluorescent response in a colourless medium of 102,500 or with reference to the x-intercept of Equation 1 a concentration of 0.037 mg/l dye. The actual level of dye was 37.5 μg/l and the fuel a mixture of Motor Spirit and UK 95 octane gasoline. Simply comparing the fluorescence of the dye with the fluorescence of the dye in a medium of zero absorbance would have predicted 0.025 mg/l.

Thus by correlating the fluorescent response of a taggant, after having quenched it selectively, with the absorbance of the medium in which it is dissolved, we have significantly improved the method for quantifying that fluorescent taggant, especially when the medium in which it is dissolved has unknown fluorescence and absorbance.

Although the invention is illustrated and described herein with reference to specific embodiments, the invention is not intended to be limited to the details shown. Rather, various modifications may be made in the details within the scope and range of equivalents of the claims and without departing from the invention.

The invention claimed is:

1. A method of measuring the fluorescence of a fluorescent marker compound dissolved or dispersed in a bulk material comprising the steps of:
   (a) measuring a characteristic of the fluorescence of a mixture of said bulk material and said fluorescent marker compound;
   (b) quenching the fluorescence of the fluorescent marker compound to produce a quenched mixture;
   (c) measuring the characteristic of the fluorescence of the quenched mixture;
   (d) comparing the fluorescent characteristic of the mixture with the fluorescent characteristic of the quenched mixture; and
   (e) correcting the measured fluorescent emission characteristic for the effects of the absorbance of the bulk material.

2. The method according to claim 1, wherein the bulk material is a liquid.

3. The method according to claim 1, wherein said fluorescent marker compound is of a chemical class selected from the group consisting of phthalocyanines, naphthalocyanines, nickel dithiolenes, aminium compounds, methine dyes, azulene quadratic acid dyes, fluorescein and derivatives thereof, substituted anthraquinones, azo dyes, porphyrins, coumarin, substituted coumarins (including umbelliferones), benzopyran and derivatives thereof, xanthene dyes (including rhodamines), oxazines, croconium dyes, naphthalimides, naphthofluorones, seminaphthofluorones, tricarbocyanines, bisindolylmaleimides, 1,3 diaryl-2-pyrazolines, 1,3,5-triaryl -2-pyrazolines, acridines, phenanthridines, and dipyrromethenes.

4. The method according to claim 1, wherein the quenching is effected by means of heat 5. The method according to claim 1, wherein the quenching of the fluorescent compound is effected by the addition of a chemical quenching compound.

6. The method according to claim 5, wherein said quenching compound is selected from the group consisting of polyoxometallate salts, potassium thiocyanate, N-chlorosuccinimide, amines, quaternary ammonium hydroxides, diazabicyclooctane, trichlorocyanuric acid, peracetic acid, peroxides, substituted anilines, substituted nitrobenzenes, soluble transition metal complexes, chlorine and hypochlorites.

7. The method according to claim 1, wherein the fluorescent emission of the quenched mixture at least one wavelength is subtracted from that of the unquenched mixture in order to correct for the fluorescent emission from the bulk material.

8. The method according to claim 1, wherein the measured fluorescent emission characteristic is corrected for the effects of the absorbance of the bulk material by means of a calibration obtained by measuring the fluorescent emission characteristic of the same fluorescent compound at the same concentration in differently coloured materials.

9. The method according to claim 8, wherein the corrected emission is compared with the emission of a standard sample of a similar marked mixture.

10. A method of identifying a bulk material comprising the step of adding to said bulk material a marker comprising at least one fluorescent compound to form a mixture of said bulk material and the fluorescent marker compound and, subsequently, measuring the fluorescence of said at least one fluorescent compound in a sample of said bulk material using the method of measuring fluorescence according to claim 1.

11. The method according to claim 1, wherein the quenching is effected by changing the pH of the mixture.

12. The method according to claim 1, wherein the quenching is effected by changing the polarity of the mixture.

13. The method according to claim 1, wherein the quenching is effected by addition of an oxidising agent.

14. The method according to claim 1, wherein the quenching is effected by addition of a reducing agent.

* * * * *